US008190244B2

(12) United States Patent
Rollins et al.

(10) Patent No.: US 8,190,244 B2
(45) Date of Patent: May 29, 2012

(54) GATED OPTICAL COHERENCE TOMOGRAPHY (OCT) ENVIRONMENTAL CHAMBER

(75) Inventors: Andrew Rollins, Highland Heights, OH (US); Michael Jenkins, Parma, OH (US); Osman Chughtai, Canton, OH (US)

(73) Assignee: Case Western Reserve University, Cleveland, OH (US)

( * ) Notice: Subject to any disclaimer, the term of this patent is extended or adjusted under 35 U.S.C. 154(b) by 1163 days.

(21) Appl. No.: 12/009,992

(22) Filed: Jan. 23, 2008

(65) Prior Publication Data
US 2008/0221445 A1 Sep. 11, 2008

Related U.S. Application Data

(60) Provisional application No. 60/886,273, filed on Jan. 23, 2007.

(51) Int. Cl.
*A61B 6/00* (2006.01)
(52) U.S. Cl. ........ 600/476; 356/496; 356/497; 356/498; 382/128
(58) Field of Classification Search .................. 600/428, 600/476; 356/496–498; 382/128
See application file for complete search history.

(56) References Cited

U.S. PATENT DOCUMENTS

| | | | |
|---|---|---|---|
| 6,697,667 B1 * | 2/2004 | Lee et al. | 600/479 |
| 6,922,580 B2 * | 7/2005 | DeMeester et al. | 600/413 |
| 2002/0146817 A1 * | 10/2002 | Cannon et al. | 435/289.1 |
| 2002/0149628 A1 * | 10/2002 | Smith et al. | 345/848 |
| 2005/0187587 A1 * | 8/2005 | Burrell et al. | 607/27 |
| 2007/0229801 A1 * | 10/2007 | Tearney et al. | 356/73 |

OTHER PUBLICATIONS

Yazdanfar, S., et al., High Resolution imaging of in vivo cardiac dynamics using color Doppler optical coherence tomography, Optics Express, vol. 1, No. 13, pp. 424-431, (1997).*
Yang, Y., et al, Cardiac PET imaging in mice with simultaneous cardiac and respiratory gating, Physics in Medicine and Biology, 50, (2005), pp. 2979-2989.*
Huber, R. et al, Three-dimensional and C-Mode OCT imaging with a compact, frequency swept laser source at 1300 nm, Optics Express, vol. 13, No. 26, pp. 10523-10538, (2005).*
Choma, M.A., et al, Spectral-domain phase microscopy, Optics Letters, vol. 30, No. 10, pp. 1162-1164, (2005).*
Jones, E.A.V., et al, Dynamic In Vivo Imaging of Postimplantation Mammalian Embryos Using Whole Embryo Culture, Genesis, 34 :228-235 (2002).*

* cited by examiner

*Primary Examiner* — Brian Casler
*Assistant Examiner* — Daniel Huntley
(74) *Attorney, Agent, or Firm* — Tarolli, Sundheim, Covell & Tummino LLP (57) ABSTRACT

Systems, methods, and other embodiments associated with gated optical coherence tomography (OCT) are described. One example method includes generating an image control signal to control an OCT apparatus to acquire an image of an embryonic heart at a specified point in time during a cardiac cycle of the embryonic heart. The method may also include controlling the OCT apparatus to acquire the image based on the image control signal. In different examples, the image may be acquired in vivo or from an excised heart that is paced. The OCT apparatus and the embryonic heart may be housed in an environmental chamber having a set of controllable environmental factors. Therefore, the method may include detecting and controlling the set of controllable environmental factors.

31 Claims, 10 Drawing Sheets

GATED OPTICAL COHERENCE TOMOGRAPHY (OCT) ENVIRONMENTAL CHAMBER

PRIORITY CLAIM

This application claims the benefit of U.S. Provisional Patent Application 60/886,273, titled "Gated Optical Coherence Tomography and Related Environmental Chamber", filed Jan. 23, 2007, which is incorporated herein by reference. The provisional application incorporated by reference papers that describe portions of the technology described herein. For example, one Applicant is an author of "4D Embryonic Cardiography Using Gated Optical Coherence Tomography," Optics Express, Vol. 14, Issue 2, pp. 736-748. Similarly, one Applicant is an author of "In vivo video rate optical coherence tomography," Opt Express 3, 219-229 (1998). Additionally, one Applicant is an author of "Quasi-telecentric optical design of a microscope-compatible OCT scanner," Opt Express 13, 6407-6415 (2005).

FEDERAL FUNDING NOTICE

The invention was developed with federal funding supplied under Federal Grant No. 1RO1 HL08304 and Federal Grant No. CO6 RR1246-01, provided by the NIH. The Federal government has certain rights in the invention.

TECHNICAL FIELD

This application describes systems and methods for performing gated optical coherence tomography (OCT). More particularly, this application describes systems and methods for in vivo four-dimensional (4D) imaging of an embryonic heart using gated OCT. In one example, the embryonic heart and the OCT apparatus are located in an environmental chamber in which a set of environmental factors can be monitored and/or controlled. In another example, the gating depends on optical signals associated with the imaged embryonic heart.

BACKGROUND

Defects in developmental mechanisms during embryogenesis can result in congenital cardiac anomalies. Understanding normal heart development mechanisms has been limited by the inability to simultaneously detect anatomic and physiologic changes in these small (e.g., less than two millimeters) organs during substantially normal development. For example, conventional systems may not have been able to simultaneously assess structure and function of a beating embryonic heart in vivo. A beating embryonic heart has conventionally been a challenge to image in vivo because it has small dimensions and is moving.

Gated cardiac imaging involves acquiring image data according to a trigger associated with the heart cycle, whether the heart cycle is naturally occurring and/or paced. Acquiring images at specified points in time in the heart cycle facilitates mitigating motion artifacts by acquiring images when the heart tissues are not moving and/or at consistent points during the cycle. Medical imaging modalities including magnetic resonance imaging (MRI) and computed tomography (CT) have used gating to image beating adult hearts. However, these conventional systems have lacked the resolution to study pre-septated embryonic hearts in vivo. Similarly, optical projection tomography (OPT) lacks the ability to image in vivo, and confocal microscopy lacks the field of view and depth range for imaging the embryo in vivo.

SUMMARY

Example systems and methods concern gated OCT imaging of embryonic hearts. Imaging apparatus acquire data to facilitate simultaneously assessing structure and function of embryonic hearts. Example systems and methods may image embryonic hearts at early stages of development. For example, embryonic avian and murine heart may be imaged as early as at stage 13. Example systems and methods facilitate in vivo embryonic cardiac imaging that includes performing a series of gated OCT data acquisition scans, where the gating depends on the cardiac cycle of the imaged embryonic heart. The cardiac cycle may be monitored using, for example, electrical, mechanical, and/or optical sensors. A signal received from a monitor may control production of a signal that controls OCT imaging apparatus to acquire an image at a desired point in time.

In one example, OCT apparatus may be housed in an environmental chamber. The environmental chamber may be fabricated to facilitate monitoring and/or controlling environmental factors including temperature, pressure, humidity, electrical fields, oxygen level, and so on. An embryonic heart to be imaged may be placed in the environmental chamber and environmental factors may be controlled to mitigate issues associated with conventional imaging systems. In one example, a gated cardiac imaging system acquires four dimensional (4D) image sets of the heart. The 4D image sets are built up over a set of heart cycles. These 4D image sets are used to calculate anatomical and physiological parameters (e.g. wall thickness, ejection fraction).

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

The following includes definitions of selected terms employed herein. The definitions include various examples and/or forms of components that fall within the scope of a term and that may be used for implementation. The examples are not intended to be limiting. Both singular and plural forms of terms may be within the definitions.

"Computer-readable medium", as used herein, refers to a medium that participates in directly or indirectly providing signals, instructions and/or data. A computer-readable medium may take forms, including, but not limited to, non-volatile media, and volatile media. Non-volatile media may include, for example, optical disks, magnetic disks, and so on. Volatile media may include, for example, semiconductor memories, dynamic memory, and so on. Common forms of a computer-readable medium may include, but are not limited to, a floppy disk, a flexible disk, a hard disk, a magnetic tape, other magnetic medium, a CD (compact disk), other optical medium, a RAM (random access memory), a ROM (read only memory), a memory chip or card, a memory stick, and other media from which a computer, a processor or other electronic device can read.

"Data store", as used herein, refers to a physical and/or logical entity that can store data. A data store may be, for example, a database, a table, a file, a list, a queue, a heap, a memory, a register, and so on. In different examples, a data store may reside in one logical and/or physical entity and/or may be distributed between two or more logical and/or physical entities.

"Logic", as used herein, includes but is not limited to hardware, firmware, software in execution, and/or combinations of each to perform a function(s) or an action(s), and/or to cause a function or action from another logic, method, and/or system. Logic may include a software controlled microprocessor, a discrete logic (e.g., application specific integrated circuit (ASIC)), an analog circuit, a digital circuit, a programmed logic device, a memory device containing instructions, and so on. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

Optical coherence tomography (OCT) refers to a family of techniques, including time domain and frequency domain implementations. Both time and frequency domain OT may perform continuous scanning and/or discrete array signal detection. OCT measures light reflected back from a sample of interest as a function of depth in order to image the interior structure of the sample. In one example, measures coherently gated back-reflected light with 2-15 μm resolution to a depth of 1-2 mm in cardiac tissue. The high resolution and appropriate field of view make OCT useful for studying cardiac development. One application of in vivo imaging of embryonic hearts is to measure physiological parameters such as ventricular volume, ejection fraction, stroke volume, and wall thickness. The ejection fraction (EF) represents the percent change in the ventricular volume from end diastole (relaxation) to end systole (contraction), while stroke volume is the magnitude of the change.

"Software", as used herein, includes but is not limited to, one or more computer or processor instructions that can be read, interpreted, compiled, and/or executed and that cause a computer, processor, or other electronic device to perform functions, actions and/or behave in a desired manner. "Software" does not refer to stored instructions being claimed as stored instructions per se. The instructions may be embodied in various forms including routines, algorithms, modules, methods, threads, and/or programs including separate applications or code from dynamically linked libraries.

"User", as used herein, includes but is not limited to one or more persons, software, computers or other devices, or combinations of these.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, determining, and so on, refer to actions and processes of a computer system, logic, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 1:
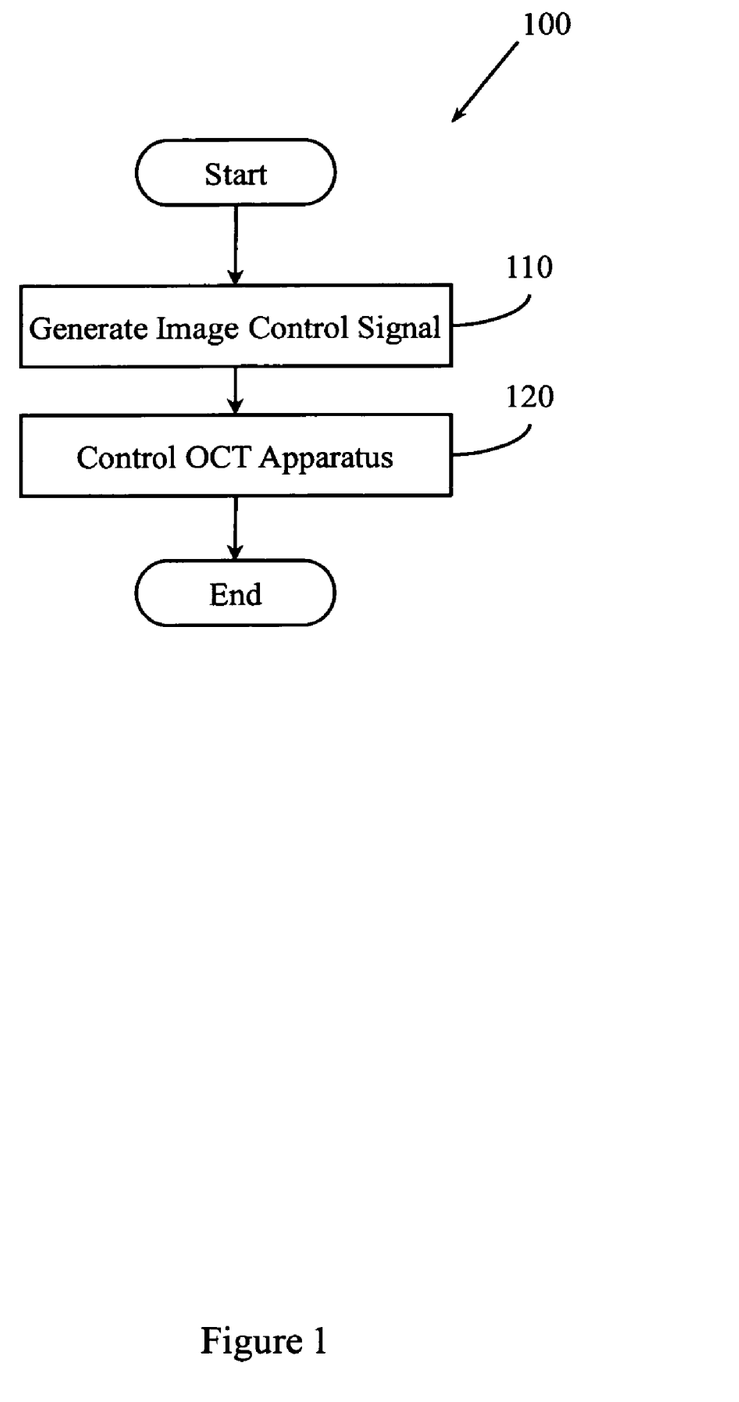
FIG. 1 illustrates an example method associated with gated OCT of embryonic heart tissue.

FIG. 1 illustrates a method 100 associated with gated OCT of embryonic heart tissue. Method 100 may include, at 110, generating an image control signal. The image control signal is used to control an OCT apparatus to acquire an image of an embryonic heart at a specified point in time during a cardiac cycle of the embryonic heart. This may be referred to as gated OCT. The embryonic heart may be, for example, a pre-septated heart.

Method 100 may also include, at 120, controlling the OCT apparatus to acquire the image. The apparatus may be controlled based, at least in part, on the image control signal. In one example, the image is to be acquired in vivo. In one example, method 100 may control an OCT apparatus that is housed in an environmental chamber that also houses the embryonic heart. The environmental chamber may have a set of controllable environmental factors (e.g., temperature, humidity, oxygen level). Thus, in one example, method 100 may include detecting an environmental factor(s) and/or controlling an environmental factor(s). For example, method 100 may include generating an environmental control signal and controlling a controllable environmental factor in the environmental chamber based, at least in part, on the environmental control signal. By way of illustration, method 100 may include detecting the temperature inside the environmental chamber and, based on the temperature, causing the environmental chamber to be heated or cooled to achieve and/or maintain a desired temperature. Environmental factors may include, for example, combinations of temperature, pressure, humidity, electrical field, magnetic field, oxygen level, atmospheric constitution, illumination, and so on.

Figure 2:
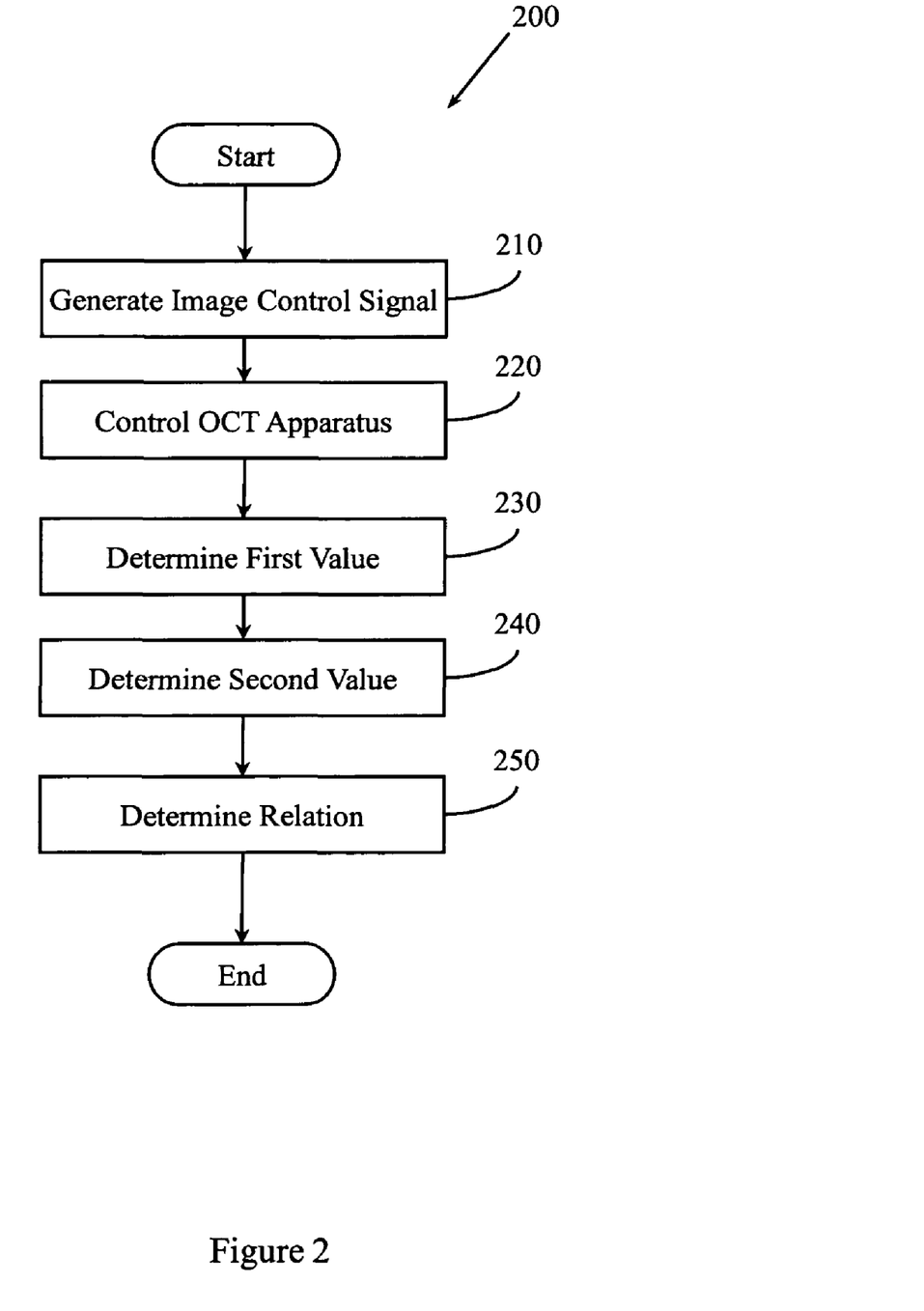
FIG. 2 illustrates another example method associated with gated OCT of embryonic heart tissue.

FIG. 2 illustrates a method 200 associated with gated OCT of embryonic heart tissue. Method 200 includes some actions similar to those described in connection with method 100 (FIG. 1). For example, method 200 includes generating an image control signal at 210 and controlling an OCT apparatus at 220. However, method 200 includes additional actions.

Method 200 may include, at 230, determining a first value associated with a structure in the embryonic heart. The first value may be determined by measuring a structure in the embryonic heart. The measurement may be taken, for example, from the image(s) acquired by the OCT apparatus. In one example, the first value may be a ventricular volume, a myocardial wall thickness, and so on.

Wall thickness may be measured, for example, from transverse optical sections through the embryonic chick heart. Segmenting the inner volume from the myocardium in a range of B-scans for a specific volume of scans may include thresholding and seeded region growing in 2D to demarcate the myocardium from the cardiac chamber. Radial lines may be drawn from the center point of the section and thus "wall thickness" is defined as the distance from the intersection of the radial line with the inner surface to the intersection of the radial line with the outer surface.

Method 200 may also include, at 240, determining a second value associated with a function of the embryonic heart. The second value may be determined by measuring a function of the embryonic heart. The measurement may also be taken and/or derived from the image(s) acquired by the OCT apparatus. In one example, the second value may be an ejection fraction, a stroke volume, and so on.

Accurate physiological measurement of ejection fraction considers structural, electrophysiological and motility characteristics of the imaged early stage hearts. When the embryonic hearts are field stimulated, the terms systole (representing end-contraction in a normally beating heart) and diastole (representing end-relaxation in a normally beating heart) are not appropriate. Instead, the terms end contraction and end-relaxation may be appropriate.

Ventricular volume may be manually segmented. To aid in determining the true ventricular cavity surface during manual segmentation, a scanning micrograph and 2D movies of the slices (B-scans) in question may be employed. Ventricular volume is defined as the entire volume of the combined ventricle. Ejection fraction may be measured from a partial volume of the ventricular chamber for the earlier stage hearts (13 and 15) corresponding to a bolus volume. Partial volume may be identified as an area of ventricular cavity that was maximally contracted after pacing, but maximally expanded after the contraction ceased. Ejection fraction may be calculated as follows: [(End-relaxation volume−End-contraction volume)/End-relaxation volume].

Method 200 may also include, at 250, determining a relationship between the first value and the second value. Example methods may perform image processing to digitally section a beating embryonic heart. In different examples the beating may be natural (in vivo imaging) or paced (excised heart). This in turn facilitates visualizing three-dimensional internal embryonic structures of the heart from different orientations during contraction and relaxation. Example methods facilitate directly measuring internal volumes and myocardial wall thicknesses during embryonic cardiac contraction and relaxation. This in turn facilitates directly measuring embryonic ejection fraction at different stages of development. Thus, determining the relationship at 250 may include examining both pre and post-processed image data.

Example methods facilitate measuring embryonic heart ejection fraction from volumetric data, as opposed to extrapolation from 2D data. Therefore, example methods provide developmental cardiology researchers with an imaging tool having temporal resolution, spatial resolution, and field of view sufficient to assess early embryonic cardiac function.

Figure 3:
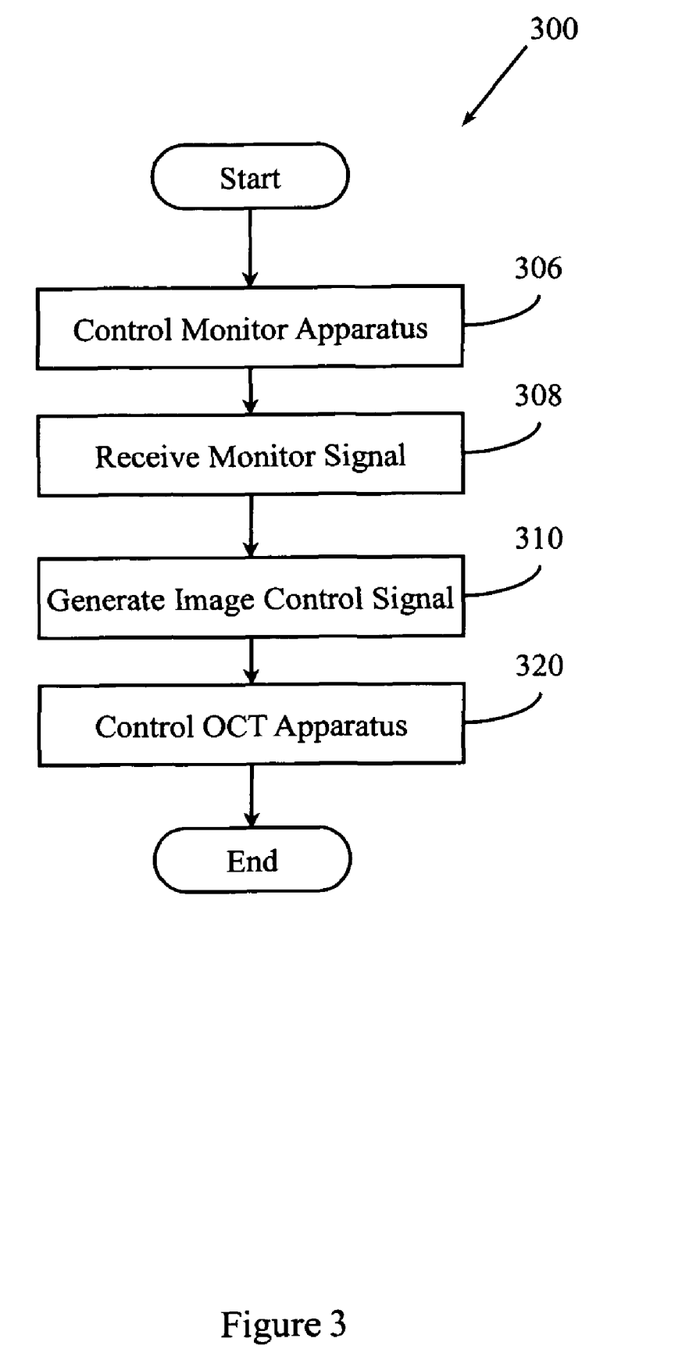
FIG. 3 illustrates another example method associated with gated OCT of embryonic heart tissue.

FIG. 3 illustrates a method 300 associated with gated OCT of embryonic heart tissue. Method 300 includes some actions similar to those described in connection with method 100 (FIG. 1). For example, method 300 includes generating an image control signal at 310 and controlling an OCT apparatus at 320. However, method 300 includes additional actions that may be performed before the OCT apparatus is controlled.

For example, method 300 may include, at 306, controlling a monitor apparatus to provide a monitor signal associated with the embryonic heart cycle. The monitor signal may be used to generate the image control signal. The monitor signal may indicate when a heart is about to contract or relax, which may in turn determine an attribute(s) of the control signal and/or when the control signal will provided. The monitor may be, for example, an electrical sensor, a mechanical sensor, an optical sensor, and so on. Electric signals may be used for cardiac gated imaging but such use has proven to be a challenge with early embryos. Thus, in one example, the monitor is a laser Doppler velocimetry (LDV) sensor that identifies blood flow indicative of the cardiac cycle of the embryonic heart. While LDV is described, it is to be appreciated that other sensors may also identify this type of blood flow. For example, optical and otherwise non-invasive sensing methods including video microscopy, confocal microscopy, optical scattering, ultrasound biomicroscopy, and so on may be employed. These optical and otherwise non-invasive techniques may be used to optically record a heart rate to facilitate controlling gated image acquisition. In one example, the monitor may be coupled to a blood vessel outside the embryonic heart. It is to be appreciated that other monitors may be positioned in other locations.

Figure 4:
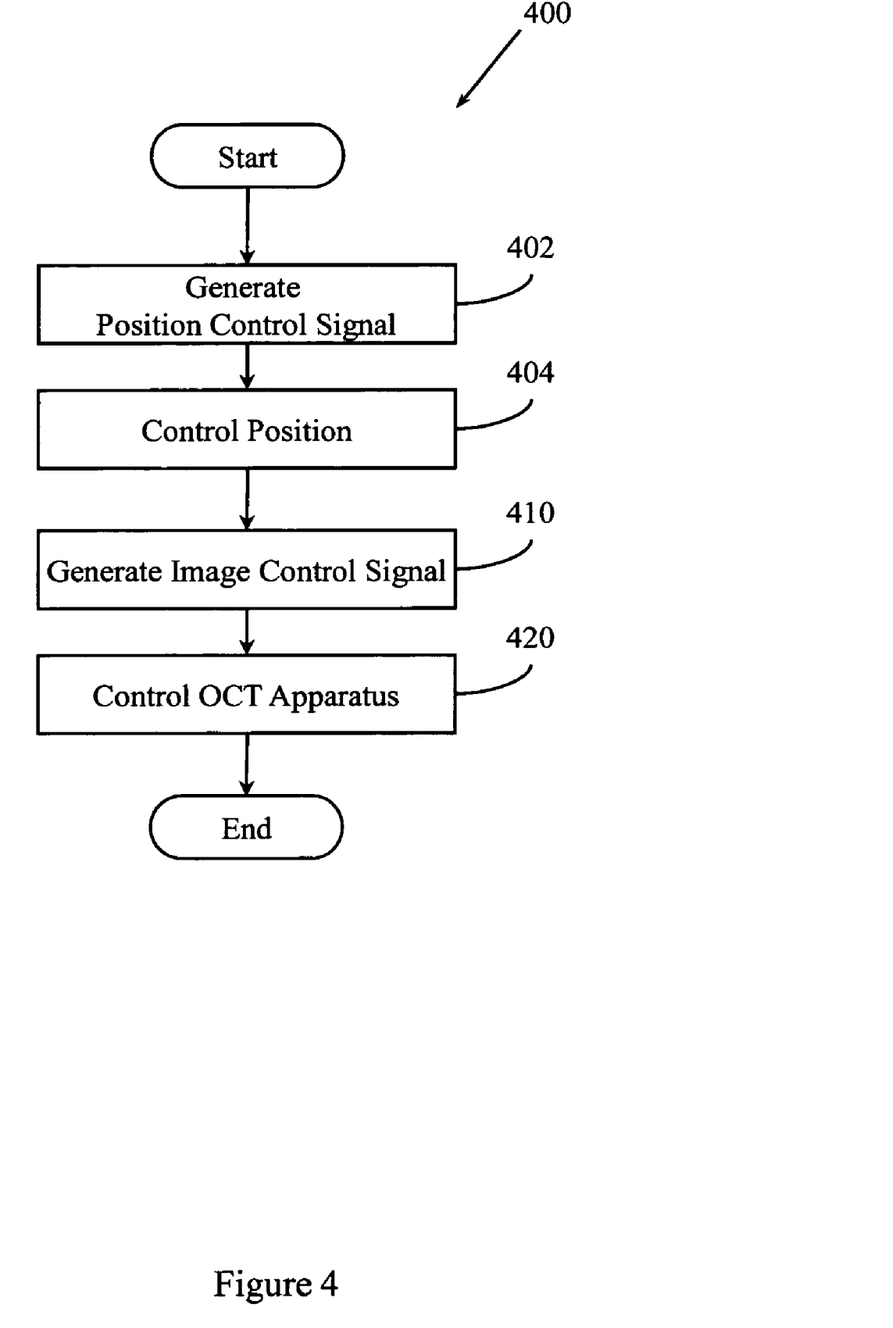
FIG. 4 illustrates an example method associated with gated OCT of embryonic heart tissue.

FIG. 4 illustrates a method 400 associated with gated OCT of embryonic heart tissue. Method 400 includes some actions similar to those described in connection with method 100 (FIG. 1). For example, method 400 includes generating an image control signal at 410 and controlling an OCT apparatus at 420. However, method 400 includes additional actions performed before the OCT apparatus is controlled at 420.

For example, method 400 may include, at 402, generating a position control signal. The position control signal is to position the OCT apparatus. The OCT apparatus may need to be moved closer to or farther from the embryonic heart, may need to be rotated around the heart, may need to be re-oriented, and so on. In one example, the position control signal is based, at least in part, on a distance measurement relating the OCT apparatus and the embryonic heart. The distance measurement may be provided, for example, by a microscope attached to and/or otherwise associated with the OCT apparatus. For example, the OCT apparatus may be positioned in an arm onto which the microscope has also been attached.

Method 400 may also include, at 404, controlling the position of the OCT apparatus based on the position control signal. While actions 402 through 420 are illustrated occurring a single time in a single sequence, it is to be appreciated that an OCT apparatus may acquire a series of images and thus method 400 may repeat actions 402 through 420 a number of times. In one example, the OCT apparatus may be repositioned after a pre-defined and/or configurable number of acquisitions.

Figure 5:
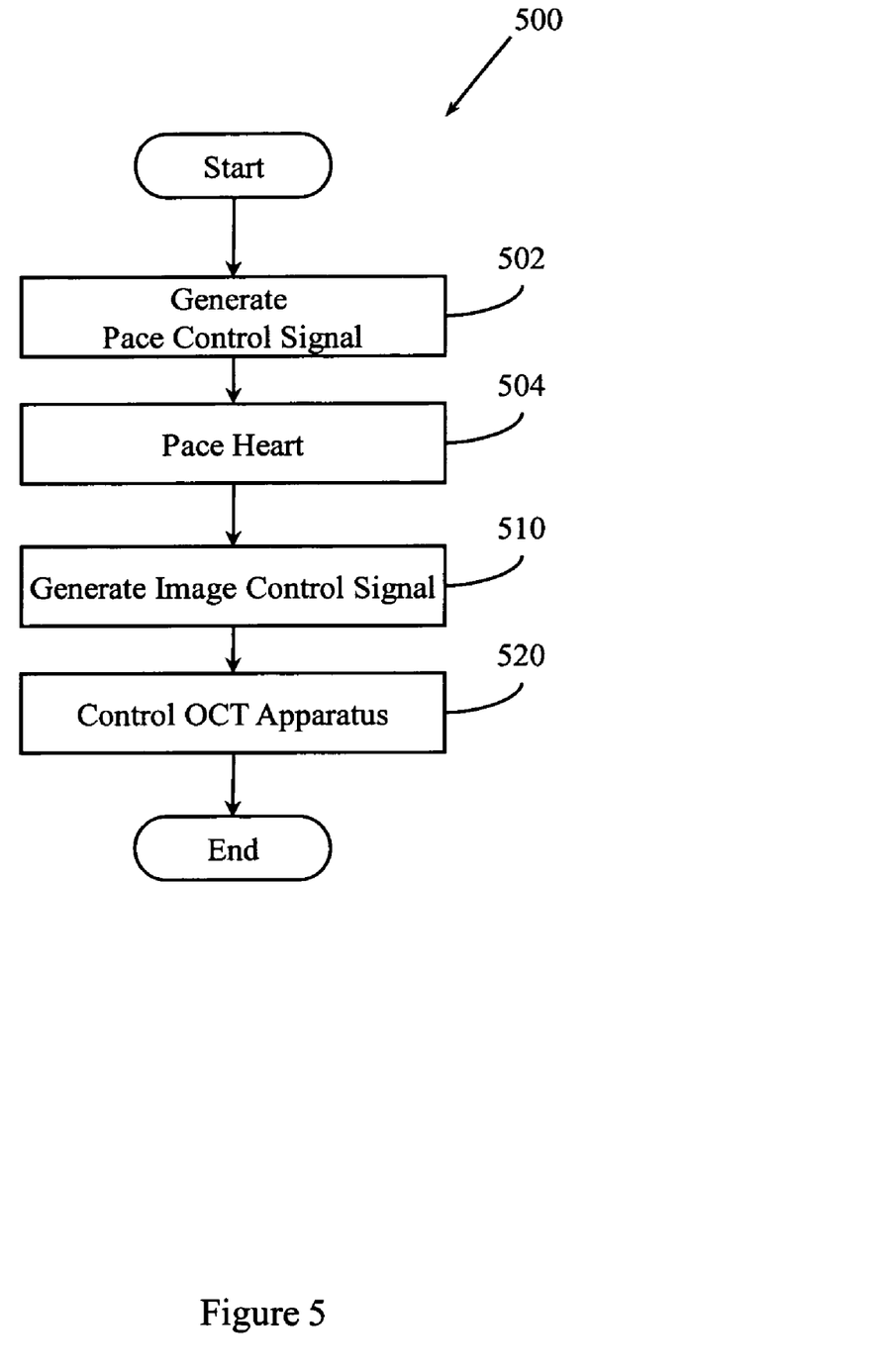
FIG. 5 illustrates another example method associated with gated OCT of embryonic heart tissue.

FIG. 5 illustrates a method 500 associated with gated OCT of embryonic heart tissue. Method 500 includes some actions similar to those described in connection with method 100 (FIG. 1). For example, method 500 includes generating an image control signal at 510 and controlling an OCT apparatus at 520. However, method 500 includes additional actions.

For example, method 500 may include, at 502, generating a pace control signal. The pace control signal may control, for example, when the embryonic heart will contract, when the embryonic heart will relax, and so on. With the pace control signal available, method 500 may also include, at 504, pacing the embryonic heart based, at least in part, on the pace control signal. While method 300 (FIG. 3) described monitoring heart activity, method 500 describes controlling heart activity. Thus, it is to be appreciated that different methods described herein may be used in different embodiments. For example, some methods may be used to acquire images in vivo, while other methods may be used to acquire images from an excised heart.

Timing circuitry, logic, and/or instrumentation may pace the heart, control beam-scanning optics, and generate data acquisition synchronization signals. A pacing pulse, frame save synchronization signal, and scanning optics control signal may be controlled using software-generated signals and a digital-to-analog converter (DAC) board in a control logic. A pacing pulse from the DAC may stimulate the heart while simultaneously triggering a first arbitrary waveform generator (AWG) to generate a series of pulses that trigger a second AWG that generated signals to drive the scanning optics and the data acquisition synchronization signal.

In one example, an electrode chamber may hold and pace the embryonic heart. One example electrode chamber includes two platinum sheets 4 cm apart embedded into a silicone pad. The electrode chamber may pace the heart with field stimulation. One example system includes a time domain system capable of capturing 4000 A-scans per second. In the example, the coherence function of the light source, which determines the axial resolution, was 14 μm full width at half maximum (FWHM) in air while the intensity profile of the incident beam, which determines the transverse resolution, was measured as 10 μm FWHM. In the example, B-scans may be acquired at 20 μm intervals to reduce imaging time. In one example, four frames may be recorded at each spatial location at each cardiac phase and then averaged to reduce noise.

Figure 6:
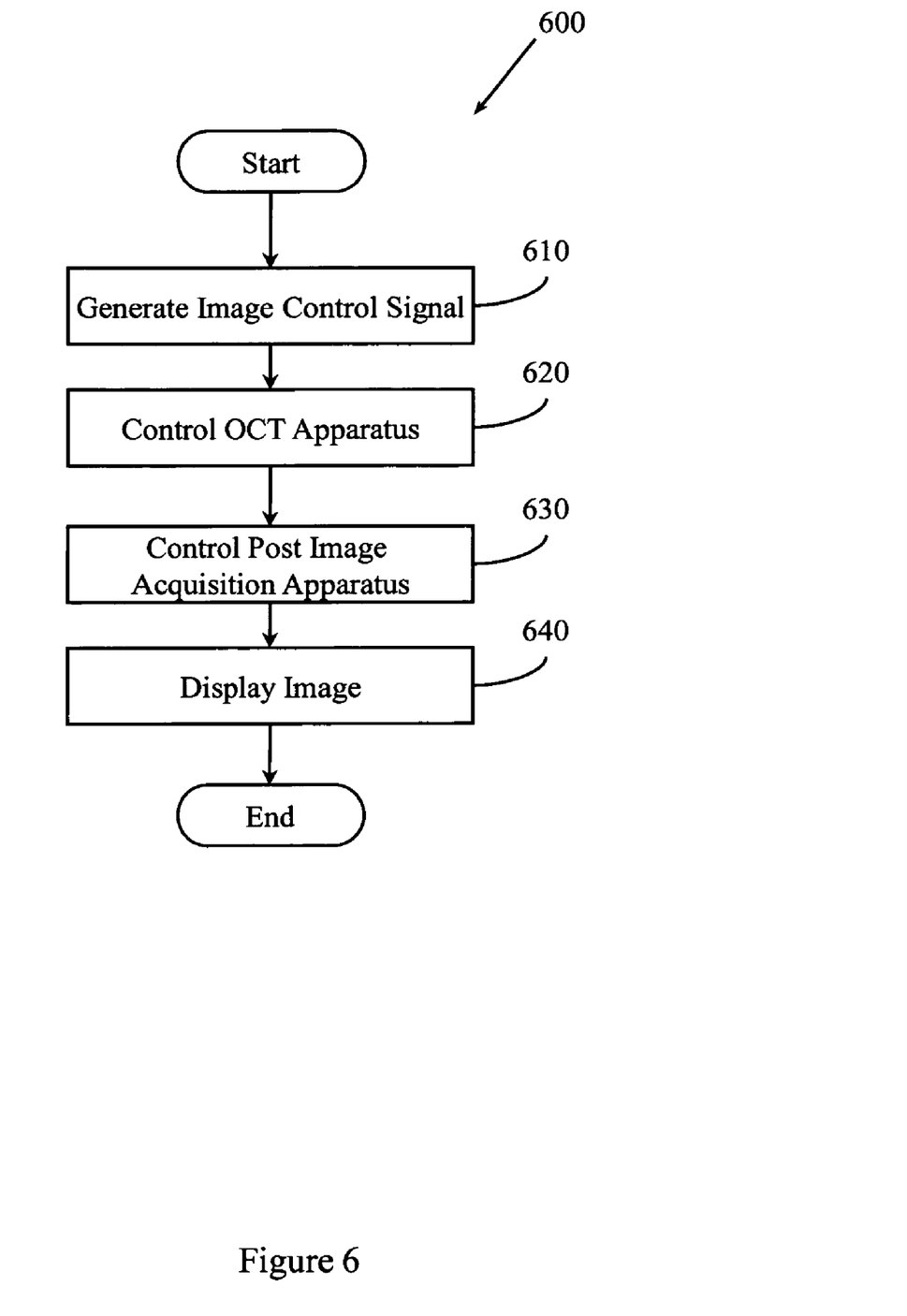
FIG. 6 illustrates another example method associated with gated OCT of embryonic heart tissue.

FIG. 6 illustrates a method 600 associated with gated OCT of embryonic heart tissue. Method 600 includes some actions similar to those described in connection with method 100 (FIG. 1). For example, method 600 includes generating an image control signal at 610 and controlling an OCT apparatus at 620. However, method 600 includes additional actions.

For example, method 600 includes, at 630, controlling an image processing apparatus to perform a post image acquisition analysis. In one example, the image(s) acquired by the OCT apparatus may be three-dimensional image. Method 600 may acquire a series of images over time to produce a 4D image, the four dimensions being x, y, z, and time series. The post image acquisition analysis may include, for example, three dimensional data visualization, and three dimensional rendering of a portion of the embryonic heart. Therefore, method 600 may also include, at 640, displaying an image. In different examples the displayed image may be a direct reproduction of acquired data or may be a processed image to which filtering, smoothing, and other image processing techniques have been applied.

In one example, 3D volumetric images of an embryo (e.g., chicken, mouse) heart are obtained in a sequence of specific temporal phases through the cardiac cycle. This example includes gating OCT image acquisition to a stimulus used to pace the heart. Images may be acquired over a set of heart cycles as the OCT field of view is translated through the heart volume. A single 3D image may be constructed by bringing together B-scans acquired at a given phase in the cardiac cycle. This may result in a 3D image that is a 'snap shot' of the heart at that phase. By generating 3D images at many sequential phases in the cardiac cycle, a 3D movie may be assembled and 3D measurements of ejection fraction may be made.

Figure 7:
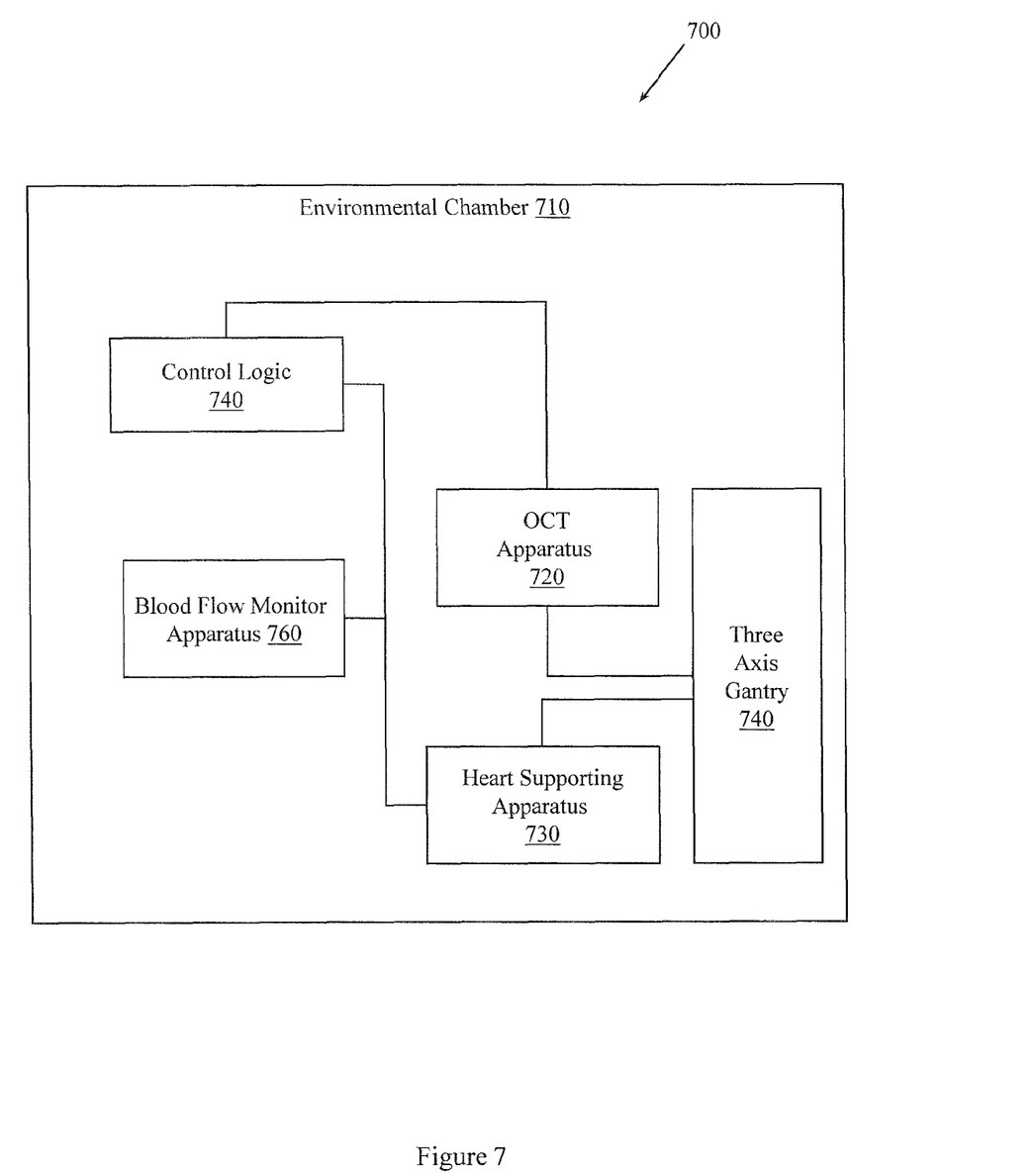
FIG. 7 illustrates an example system associated with gated OCT of embryonic heart.

FIG. 7 illustrates an apparatus 700 to acquire an image of an embryonic heart tissue in vivo. Apparatus 700 may include an OCT apparatus 720. In one example, the OCT apparatus 720 may be a gated spectral domain OCT apparatus. Apparatus 700 may also include an embryonic heart supporting apparatus 730 to support the embryonic heart. The heart supporting apparatus 730 may be, for example, a platform on which a Petri dish may be held, an electrode chamber in which a heart may be held, and so on. In one example, both the OCT apparatus 720 and the embryonic heart supporting apparatus 730 are located inside an environmental control chamber 710.

Apparatus 700 may also include a three axis gantry operably connected to either the OCT apparatus 720 and/or the heart supporting apparatus 730. The three axis gantry is to position the OCT apparatus 720 with respect to the embryonic heart supporting apparatus 730. For example, the distance between the OCT apparatus 720 and the heart supporting apparatus 730, the angle between the OCT apparatus 720 and the heart supporting apparatus 730, a rotational aspect between the OCT apparatus 720 and the heart supporting apparatus 730, and so on, may be manipulated by the three axis gantry.

Apparatus 700 may also include a control logic 740. Control logic 740 is to control the OCT apparatus 720 to acquire the image of the embryonic heart tissue in vivo at a selected point in a cardiac cycle of the embryonic heart. The control logic 740 may determine a location in the cardiac cycle of the embryonic heart and then control the OCT apparatus 720 to acquire the image at a time based, at least in part, on the determined location in the cardiac cycle. In different examples and/or at different times the control logic 740 controls the OCT apparatus 720 to image the embryonic heart tissue at, an end of contraction phase of a cardiac cycle, and an end of relaxation phase of a cardiac cycle, and at other times. One way that the control logic 740 may determine what control to exercise over the OCT apparatus 720 is by analyzing information provide by a blood flow monitor apparatus 760. Blood flow monitor apparatus 760 may monitor blood flow associated with the embryonic heart and provide a blood flow signal to the control logic 740. Blood flow monitor apparatus 760 may be, for example, an optical based device. The control logic 740 may then determine the location in the cardiac cycle of the embryonic heart based, at least in part, on the blood flow signal.

While control logic 740 is illustrated inside environmental chamber 710, it is to be appreciated that it may be located outside environmental chamber 710. Similarly, while blood flow monitor apparatus 760 is illustrated inside environmental chamber 710, it is to be appreciated that a sensor portion of apparatus 760 may be located inside chamber 710 while a processing portion of apparatus 760 may be located outside the environmental chamber 710.

In one example, apparatus 700 may perform 4D OCT imaging of early (pre-septated) avian embryo hearts in vivo with full spatial resolution. A laser Doppler velocimetry (LDV) signal from a vitelline vessel located outside the embryo may be used for gating the OCT imaging. In one example, the environmental chamber 710 may be a humidified, forced draft incubator (e.g., GQF Manufacturing). The environmental chamber 710 may be controlled to maintain 39° C. In one example, the heart supporting apparatus 730 supports a 3.6 cm diameter Petri dish. An embryo may be positioned to a central location on the top surface of the yolk and placed back in the environmental chamber 730 (e.g., incubator) until imaged. In one example, the dish containing a cultured embryo may be positioned on a temperature-controlled heating pad (37° C.) under the OCT apparatus 720. In one example, the OCT apparatus 720 may include a time-domain OCT engine that acquires 4000 A-lines per second. The apparatus 700 may also include a microscope integrated scanner. An example system may have resolution of approximately 10 um isotropically in tissue. An LDV needle probe may be positioned adjacent to a vitelline vessel. The LDV output signal may be filtered and amplified and input to a trigger generator. The trigger generator may produce a trigger at the zero-crossings of the sinusoid. The output of the trigger generator may activate an FPGA board to control the OCT imaging system. FPGA parameters may be adjusted to accommodate a range of heart rates (around 1-4 Hz).

The 4D dataset may be visualized using suitable software tools. Four images may be averaged at each position and heart-cycle phase. Aspect ratio may be corrected. Manually segmenting the heart tube from surrounding tissue in the 2D images facilitates 3D surface rendering of the heart. Sum voxel projection facilitates rapidly visualizing the 3D structure of the heart. Sum voxel projection requires no segmentation and enables evaluation of the inner structure of the heart. A visible bounding box may be added to the sum voxel projection images to facilitate interpretation of the 3D structure.

Figure 8:
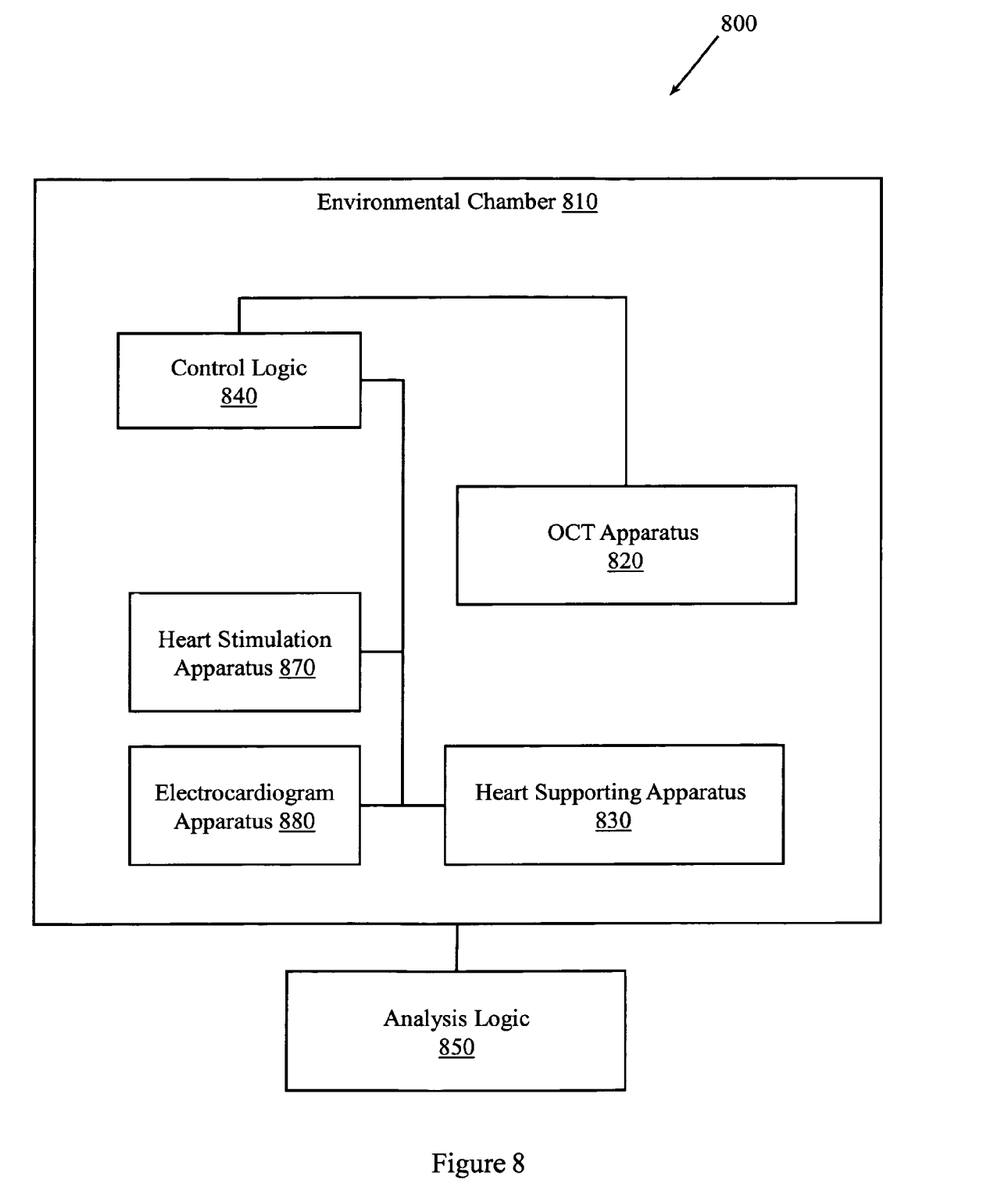
FIG. 8 illustrates another example system associated with gated OCT of embryonic heart.

FIG. 8 illustrates an apparatus 800 to acquire an image of an embryonic heart tissue in vivo. Apparatus 800 may include some elements similar to those described in connection with apparatus 700 (FIG. 7). For example, apparatus 800 may include an OCT apparatus 820, an embryonic heart supporting apparatus 830, and a control logic 840. These elements may be housed in an environmental chamber 810. However, apparatus 800 may include other elements.

For example, apparatus 800 may include an analysis logic 850. Analysis logic 850 may quantify an attribute of a structural element of the embryonic heart based, at least in part, on the image acquired by the OCT apparatus 820. Analysis logic 850 may also quantify an attribute of a functional aspect of the embryonic heart based, at least in part, on the image acquired by the OCT apparatus 820. In one example, the analysis logic 850 is to quantify an attribute of a functional aspect of the embryonic heart based, at least in part, on the image acquired by the OCT apparatus 820 and the attribute of the structural element of the embryonic heart.

Analysis logic 850 may perform post-acquisition image processing tasks. These tasks may include 3D data visualization and the measurement of physiological parameters. To reduce background noise and speckle noise, four frames at each position and phase may be temporally averaged to produce one frame to be used for 3D visualization and measurements. Images may then be cropped around the region of interest to reduce the size of the data set which facilitates reducing processing time. Because the images are characterized by an intensity fall-off in depth, which is approximately exponential in nature, an exponential correction may be applied in the axial direction. Speckle noise may further be reduced by applying a median filter. The heart may also be segmented from the background by thresholding and seeded region growing.

Creating 3D renderings of the image data for visualization purposes may include correcting aspect ratio. Gaussian filters in x, y, and z may smooth the borders of the heart. A marching cubes algorithm may transform the volume data to surface data for visualization with appropriate lighting and view angle. Movies are visualized by displaying several 3D frames in sequence with an appropriate time lag (e.g., 1/16 second) between frames.

Apparatus 800 may also include an embryonic heart stimulation apparatus 870. In one example, the heart stimulation apparatus 870 may be a pacemaker. When apparatus 800 includes heart stimulation apparatus 870, control logic 840 may control pacing of the embryonic heart by providing an electrical stimulus control signal to the embryonic heart stimulation apparatus 870. The embryonic heart stimulation apparatus 870 may then stimulate an embryonic heart to control when the heart contracts and/or relaxes. In one example, the control logic 840 is to determine a location in the cardiac cycle of the embryonic heart and, in conjunction with the heart simulation apparatus 870, to control the OCT apparatus 820 to acquire an image at a time based on the determined location in the cardiac cycle and the signal provided to the heart stimulation apparatus 870. Apparatus 700 (FIG. 7) illustrated a blood flow monitor apparatus 760 that could be used to determine a phase in the cardiac cycle of the heart. Apparatus 800 may include an electrocardiogram apparatus 880 to monitor an electrical attribute of the embryonic heart and to provide a cardiac cycle signal. In this example, the control logic 840 is to determine a location in the cardiac cycle of the embryonic heart based, at least in part, on the cardiac cycle signal.

Figure 9:
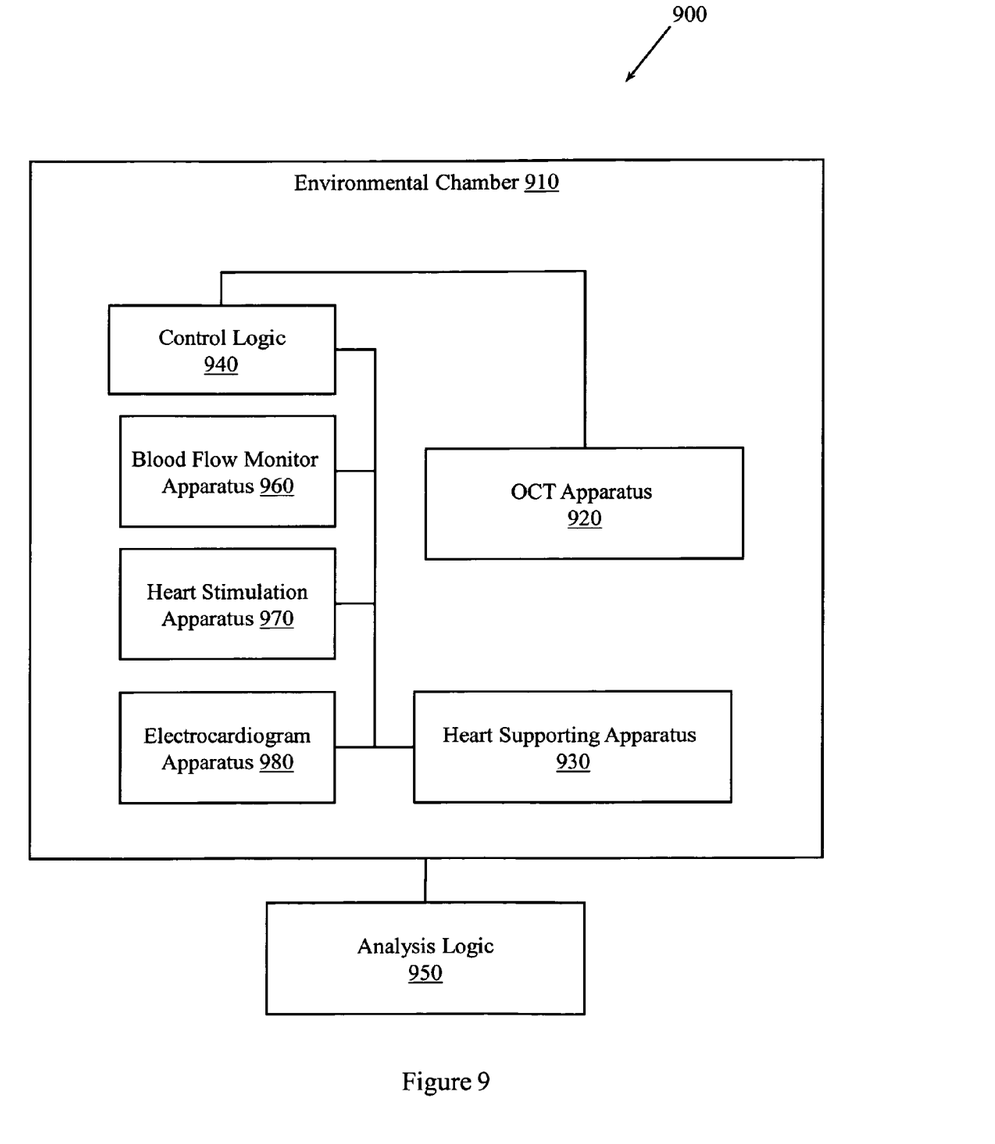
FIG. 9 illustrates another example system associated with gated OCT of embryonic heart.

FIG. 9 illustrates an apparatus 900 that includes all the elements of apparatus 700 and apparatus 800. For example, apparatus 900 includes an OCT apparatus 920, a heart supporting apparatus 930, a control logic 940, an analysis logic 950, a blood flow monitor apparatus 960, a heart stimulation apparatus 970, and an electrocardiogram apparatus 980. In this example, the control logic 940 may determine a phase in cardiac cycle using blood flow and/or electrical signals. In this example, the control logic 940 may also pace the heart based on blood flow and/or electrical signals. The control logic 940 may also control the OCT apparatus 920 to acquire images at desired times based on the signals provided by the blood flow monitor apparatus 960 and the electrocardiogram apparatus 980, and may also control the OCT apparatus 920 to acquire images at times coordinated with an electrical stimulus provided to a heart by the heart stimulation apparatus 970.

Figure 10:
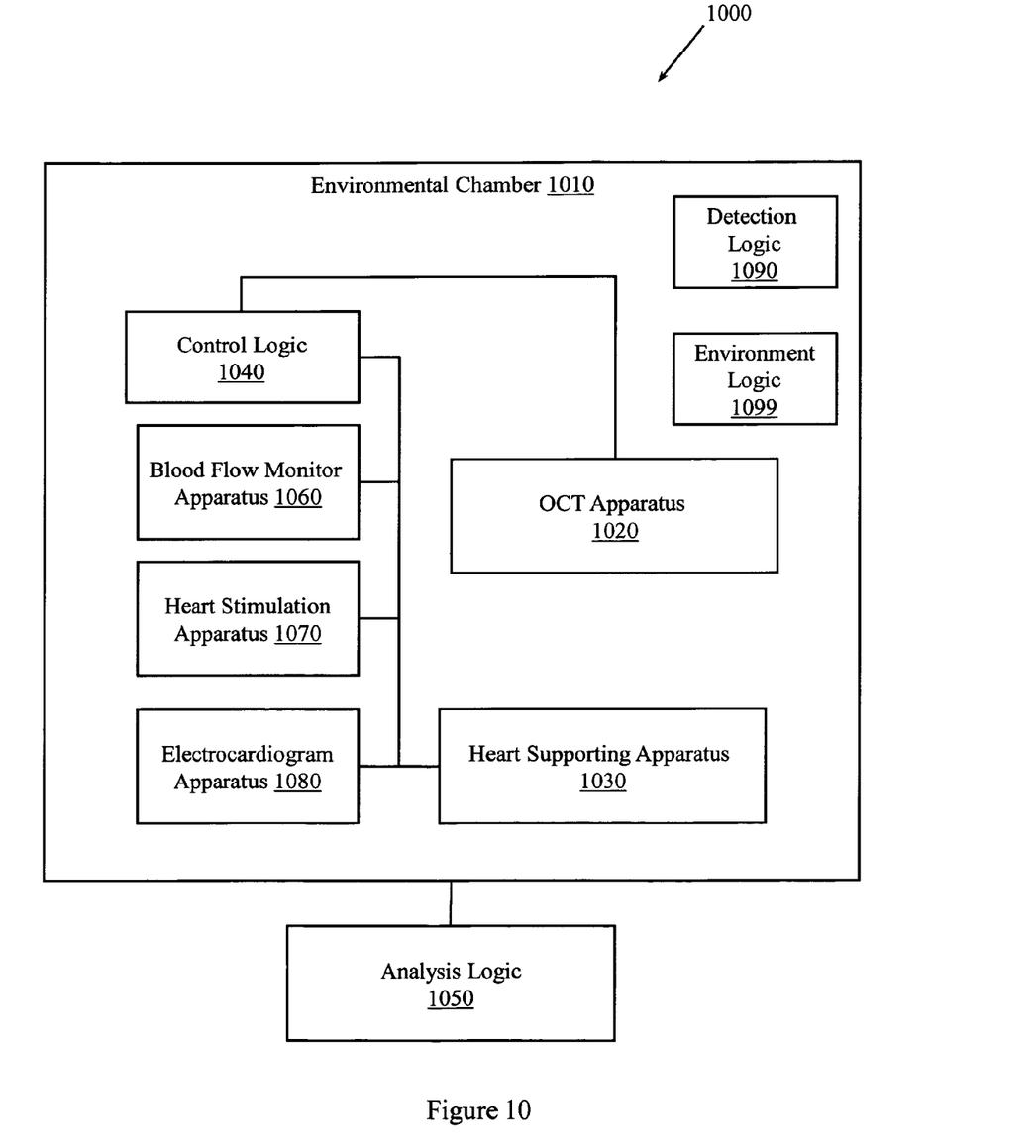
FIG. 10 illustrates another example system associated with gated OCT of embryonic heart.

FIG. 10 illustrates an apparatus 1000 that includes elements of apparatus 900. For example, apparatus 1000 includes an OCT apparatus 1020, a heart supporting apparatus 1030, a control logic 1040, an analysis logic 1050, a blood flow monitor apparatus 1060, a heart stimulation apparatus 1070, and an electrocardiogram apparatus 1080. Apparatus 1000 also includes a detection logic 1090 and an environment logic 1099.

In one example, detection logic 1090 may monitor environmental conditions inside the environmental chamber 1010. For example, detection logic 1090 may detect a temperature inside the environmental chamber 1010, an oxygen level inside the environmental chamber 1010, a humidity inside the environmental chamber 1010, and so on. Having detected an environmental condition, apparatus 1000 may seek to control a condition. Thus, the environment logic 1099 may control the temperature inside the environmental chamber 1010, the oxygen level inside the environmental chamber 1010, the humidity inside the environmental chamber 1010, and so on. While three environmental factors are described, it is to be appreciated that a greater and/or lesser number of factors may be processed. While detection logic 1090 and environment logic 1099 are illustrated inside environmental chamber 1010, it is to be appreciated that some portions of detection logic 1090 and environment logic 1099 may be located outside environmental chamber 1010. Similarly, while apparatus 1000 includes all the elements described in connection with apparatus 700 (FIG. 7), apparatus 800 (FIG. 8), and apparatus 900 (FIG. 9), it is to be appreciated that apparatus 1000 may include the detection logic 1090 and environment logic 1099 while including less than all the other elements.

In one example, the environmental chamber 1010 may have an outer enclosure having a suitable dimension, (e.g., 2' by 3' by 4'). The enclosure may have, for example, Plexiglas walls. The walls may be insulated. A three-axis gantry (e.g., Velmex gantry) may position an OCT sample arm above a Petri dish containing an embryo. A microscope may be attached to the OCT sample arm to calibrate the position of the OCT imaging apparatus. The sample arm may be enclosed in Plexiglas to, for example, protect it from humidity. A feed back temperature controller may be employed to regulate the temperature. In one example, temperature may be regulated using heating wires stretched across a heating duct. A fan may flow air past the wires and over a water tray to create humidity. The environmental chamber 1010 may include feedback oxygen and feedback control on the humidity settings.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be employed.

What is claimed is:

1. A computer-implemented method to acquire in vivo images of an embryonic heart in an ex ovo embryo, comprising:
    generating a series of image control signals to control an optical coherence tomography (OCT) apparatus to acquire, in vivo, a series of images of the embryonic heart at specified points in time during a series of cardiac cycles of the embryonic heart;
    controlling the OCT apparatus to acquire the series of images based, at least in part, on the series of image control signals;
    directly measuring, in three dimensions, from the series of images, one or more of, a ventricular volume of the embryonic heart, a myocardial wall thickness of the embryonic heart, an ejection fraction of the embryonic heart, and a stroke volume of the embryonic heart,
    where at least one of, the ventricular volume, the myocardial wall thickness, the ejection fraction, and the stroke volume is based on measurements from at least two different cardiac cycles from the embryonic heart, and
    where the OCT apparatus is configured to measure coherently gated back-reflected light at a resolution between 2-15 μm and with a penetration depth between 1-2 mm in tissue in the embryonic heart.

2. The computer-implemented method of claim 1, comprising controlling the OCT apparatus to operate in the time domain to acquire data at a rate of at least 4,000 A-lines per second.

3. The computer-implemented method of claim 1,
    where the OCT apparatus and the embryonic heart are housed in an environmental chamber having a set of controllable environmental factors; and
    where the method includes controlling the set of controllable environmental factors at a precision sufficient to sustain the ex ovo embryo in which the embryonic heart is located for at least seven days.

4. The computer-implemented method of claim 3, where the set of controllable environmental factors includes one or more of, temperature, pressure, humidity, electrical field, magnetic field, oxygen level, atmospheric constitution, and illumination.

5. The computer-implemented method of claim 1, including controlling a monitor apparatus to provide a monitor signal associated with the embryonic cardiac cycle, where the image control signal depends, at least in part, on the monitor signal.

6. The computer-implemented method of claim 5, where the monitor apparatus is one or more of, an electrical sensor, a mechanical sensor, and an optical sensor.

7. The computer-implemented method of claim 5, where the monitor apparatus is a laser Doppler velocimetry (LDV) sensor.

8. The computer-implemented method of claim 7, where the monitor signal identifies blood flow indicative of the cardiac cycle of the embryonic heart.

9. The computer-implemented method of claim 6, where the monitor is coupled to a blood vessel outside the embryonic heart.

10. The computer-implemented method of claim 6, where the monitor apparatus is an optical monitoring based apparatus configured to optically record a heart rate and where the control signal is based, at least in part, on the heart rate.

11. The computer-implemented method of claim 1, including:
generating a position control signal to position the OCT apparatus, where the position control signal is based, at least in part, on a distance measurement relating the OCT apparatus and the embryonic heart; and
controlling the position of the OCT apparatus based on the position control signal.

12. The computer-implemented method of claim 11, where the distance measurement is provided by a microscope attached to the OCT apparatus.

13. The computer-implemented method of claim 1, including:
generating a pace control signal to control one or more of, when the embryonic heart will contract, and when the embryonic heart will relax, and
pacing the embryonic heart based, at least in part, on the pace control signal.

14. The computer-implemented method of claim 1, where the image is a three-dimensional image, and where the method includes acquiring a series of images to produce a 4D image, the four dimensions being x, y, z, and time series.

15. The computer-implemented method of claim 14, including controlling an image processing apparatus to perform a post image acquisition analysis, including one or more of, three dimensional data visualization, and three dimensional rendering of a portion of the embryonic heart.

16. The computer-implemented method of claim 15, where the image is acquired at one of, an end-of-contraction phase in the cardiac cycle, and an end-of-relaxation phase in the cardiac cycle.

17. An apparatus, comprising:
an OCT apparatus configured to acquire, in vivo, an image of an embryonic heart tissue located in an embryonic heart in an embryo, where the OCT apparatus is configured to measure coherently gated back-reflected light at a resolution between 2-15 μm and with a penetration depth between 1-2 mm sufficient to measure a myocardial wall thickness in the embryonic heart tissue;
an embryo supporting apparatus to support the embryo in which the embryonic heart is located;
a three axis gantry operably connected to one of the OCT apparatus and the embryo supporting apparatus, where the three axis gantry is configured to position the OCT apparatus with respect to the embryo supporting apparatus with respect to distance, angle, and rotational aspect; and
a control logic to control the OCT apparatus to acquire the image of the embryonic heart tissue in vivo at a selected point in a cardiac cycle of the embryonic heart;
where the OCT apparatus and the embryo supporting apparatus are located inside an environmental control chamber configured to control three or more of, temperature inside the chamber, atmospheric pressure inside the chamber, humidity inside the chamber, illumination inside the chamber, oxygen content inside the chamber, atmospheric composition inside the chamber, electrical fields inside the chamber, and magnetic fields inside the chamber.

18. The apparatus of claim 17, where the OCT apparatus is a gated spectral domain OCT apparatus.

19. The apparatus of claim 17, including an analysis logic to quantify an attribute of a structural element of the embryonic heart based, at least in part, on the image.

20. The apparatus of claim 19, where the analysis logic is to quantify an attribute of a functional aspect of the embryonic heart based, at least in part, on the image.

21. The apparatus of claim 19, where the OCT apparatus operates in the time domain to acquire at least 4000 A-lines per second.

22. The apparatus of claim 17, including an analysis logic configured to directly measure, in three dimensions, from images of the embryonic heart, a ventricular volume, a myocardial wall thickness, an ejection fraction, and a stroke volume.

23. The apparatus of claim 17, including an analysis logic configured to directly measure, in three dimensions, from images of the embryonic heart, a wall thickness of the embryonic heart, where the wall thickness is measured using transverse optical sections through the embryonic heart, and where the wall thickness is computed as the distance between an intersection of a radial line with an inner surface of the embryonic heart and an intersection of the radial line with an outer surface of the embryonic heart.

24. The apparatus of claim 17, including an analysis logic configured to measure embryonic heart ejection fraction from volumetric data acquired by directly measuring an internal volume during contraction and relaxation of the embryonic heart.

25. The apparatus of claim 17, including an embryonic heart stimulation apparatus, and where the control logic is to pace the embryonic heart by providing an electrical stimulus control signal to the embryonic heart stimulation apparatus.

26. The apparatus of claim 17, where the control logic is to determine a location in the cardiac cycle of the embryonic heart and where the control logic is to control the OCT apparatus to acquire the image at a time based, at least in part, on the determined location in the cardiac cycle.

27. The apparatus of claim 26, including an optical blood flow monitor apparatus to optically monitor blood flow associated with the embryonic heart and to provide a blood flow signal, and where the control logic is to determine the location in the cardiac cycle of the embryonic heart based, at least in part, on the blood flow signal.

28. The apparatus of claim 26, including an electrocardiogram apparatus to monitor an electrical attribute of the embryonic heart and to provide a cardiac cycle signal, and where the control logic is to determine a location in the cardiac cycle of the embryonic heart based, at least in part, on the cardiac cycle signal.

29. An apparatus, comprising:
an OCT apparatus configured to acquire an image of an embryonic heart tissue located in an excised embryonic heart, where the OCT apparatus is configured to measure coherently gated back-reflected light at a resolution between 2-15 μm and with a penetration depth between 1-2 mm sufficient to measure a myocardial wall thickness in the embryonic heart tissue;
an embryonic heart supporting apparatus to support the embryonic heart;
a three axis gantry operably connected to one of the OCT apparatus and the embryonic heart supporting apparatus, where the three axis gantry is configured to position the OCT apparatus with respect to the embryonic heart supporting apparatus with respect to distance, angle, and rotational aspect; and
a control logic to control the OCT apparatus to acquire the image of the embryonic heart tissue at a selected point in a cardiac cycle of the embryonic heart;
where the OCT apparatus and the embryonic heart supporting apparatus are located inside an environmental control chamber configured to control three or more of, temperature inside the chamber, atmospheric pressure inside the chamber, humidity inside the chamber, illumination inside the chamber, oxygen content inside the chamber, atmospheric composition inside the chamber, electrical fields inside the chamber, and magnetic fields inside the chamber.

30. An apparatus for performing in vivo three dimensional image processing of an ex ovo, beating, developing, embryonic heart, comprising:

an incubator;

an OCT apparatus, where at least a sample arm of the OCT apparatus is located in the incubator, and where the OCT apparatus is configured to operate in both the time domain and frequency domain and to be able to acquire data with a resolution of at least 5 um and a penetration depth of at least 1.5 mm;

a microscope attached to the sample arm of the OCT apparatus; and logic configured to facilitate four dimensional visualization of an internal structure of the embryonic heart at specified points of a cardiac cycle of the embryonic heart, where the four dimensional visualization is sufficient to detect anatomic and physiologic changes associated with rapid, complex morphogenesis of the embryonic heart.

31. An apparatus for performing in vivo three dimensional image processing of an excised embryonic heart, comprising:

an incubator;

an OCT apparatus, where at least a sample arm of the OCT apparatus is located in the incubator, and where the OCT apparatus is configured to operate in both the time domain and frequency domain and to be able to acquire data with a resolution of at least 5 um and a penetration depth of at least 1.5 mm;

a microscope attached to the sample arm of the OCT apparatus; and logic configured to facilitate four dimensional visualization of an internal structure of the embryonic heart at specified points of a cardiac cycle of the embryonic heart, where the four dimensional visualization is sufficient to directly measure one or more of, a thickness of a wall in the embryonic heart, an internal structure of the embryonic heart, and an internal volume of the embryonic heart.

* * * * *